United States Patent [19]

Lacolle et al.

[11] Patent Number: 4,659,741
[45] Date of Patent: Apr. 21, 1987

[54] β-[2-(HALOGENOBENZYL)-PHENOXY]-ETHYLAMINE DERIVATIVES

[75] Inventors: Jean-Yves Lacolle, La Celle St Cloud; Bernard Danree, Poissy, both of France

[73] Assignee: Institut de Recherches Chimiques et Biologiques Appliquees (I.R.C.E.B.A), Paris, France

[21] Appl. No.: 675,297

[22] Filed: Nov. 27, 1984

[30] Foreign Application Priority Data

Nov. 29, 1983 [FR] France ................. 83 19056

[51] Int. Cl.⁴ ..................... A61K 31/14; C07C 87/30
[52] U.S. Cl. ..................... 514/643; 514/648; 564/283; 564/324
[58] Field of Search ............. 564/283, 324; 514/643, 514/648

[56] References Cited

U.S. PATENT DOCUMENTS

| | | | |
|---|---|---|---|
| 2,673,879 | 3/1954 | Mills et al. | 564/324 |
| 2,681,933 | 6/1954 | Wheatley | 564/324 |
| 3,488,357 | 1/1970 | Bencze | 564/283 |
| 3,855,317 | 12/1974 | Debat | 568/745 |
| 3,984,482 | 10/1976 | Debat | 568/745 |
| 4,024,282 | 5/1977 | Kikumoto et al. | 564/324 |
| 4,562,211 | 12/1985 | Kikumoto et al. | 514/648 |

FOREIGN PATENT DOCUMENTS

| | | | |
|---|---|---|---|
| 504409 | 7/1951 | Belgium. | |
| 2372792 | 12/1977 | France. | |
| 998286 | 7/1965 | United Kingdom | 564/324 |

OTHER PUBLICATIONS

Cheney et al., J. Am. Chem. Soc., vol. 71, pp. 60–64, (1949).
The Journal of Organic Chemistry, vol. 20, pp. 1129–1134 (1955).

Primary Examiner—Natalie Trousof
Assistant Examiner—Bruce D. Gray
Attorney, Agent, or Firm—Burgess, Ryan & Wayne

[57] ABSTRACT

This invention is concerned with new β-[2-(halogenobenzyl)-phenoxy]-ethylamine derivatives of the general formula

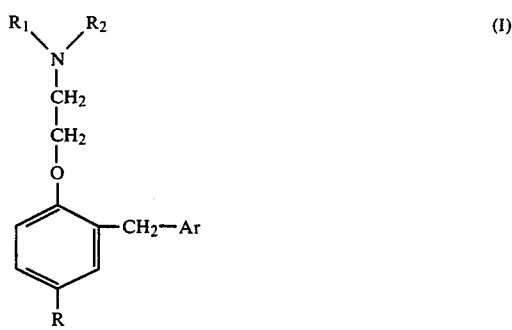

wherein
R represents a $C_1$–$C_8$-alkyl group having a linear or branched hydrocarbon chain,
$R_1$ and $R_2$, which may identical or different, represent each a $C_1$–$C_4$-alkyl-group, and
Ar represents a polychlorophenyl group of the formula

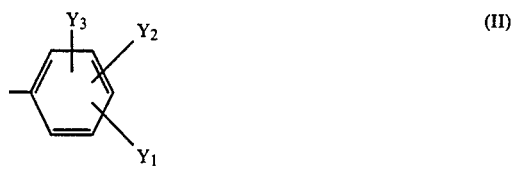

(in which $Y_1$ is 4-Cl, $Y_2$ is H or Cl, and $Y_3$ is H or Cl, at least one of the $Y_2$ and $Y_3$ being Cl); and their addition salts.

These new compounds are useful as pharmaceuticals.

11 Claims, No Drawings

β-[2-(HALOGENOBENZYL)-PHENOXY]-ETHYLAMINE DERIVATIVES

This invention relates to β-[2-(halogenobenzyl)-phenoxy]-ethylamine derivatives as new industrial products. It also relates to the method of preparation of said products and their use as pharmaceuticals.

It is known that in the past 2-(halogenobenzyl)-4-alkylphenols (wherein the 4-alkyl group is a branched hydrocarbon radical, in particular an isopropyl, s-butyl, t-butyl, or 1,1,3,3-tetramethylbutyl radical) have been proposed as bacteriostatic substances in U.S. Pat. Nos. 3,830,852; 3,855,317; 3,984,482 and in BUU-HOI et al., J. Org. Chem., 20, pages 1129–1134 (1955).

It is known that 2-(2,4-dichlorobenzyl)-4-(1,1,3,3-tetramethylbutyl)-phenol (which is coded as "B.11" and which is disclosed in the example 1 of U.S. Pat. No. 3,830,852) has been commercialized in France as an anti-infectious drug (International Common Denomination: "CLOFOCTOL"; trademark of the speciality: "OCTOFENE"). This compound, which is particularly effective in the treatment of infectious diseases caused by Gram+ bacteriae, and its analogues of the 2-(halogenobenzyl)-4-alkylphenol type are not naturally water soluble nor water dispersible. The poor affinity for water of said 2-(halogenobenzyl)-4-alkylphenols constitutes a drawback which restricts their use from a galenical point of view.

Moreover it is known that monohalogenated derivatives of β-[2-(halogenobenzyl)-phenoxy]-ethylamine have been disclosed or suggested in the past. In particular the above cited BUU-HOI et al. article discloses as chemical compounds the β-[2-(4-chlorobenzyl)-phenoxy]-N,N-dimethyl-ethylamine and its hydrochloride, and, BE-A-504 409 includes within its general formula acid addition salts of β-[2-(monohalogenobenzyl)-4-(lower)alkyl-phenoxy]-N,N-dialkylethylamine, but the sole compound which is specifically disclosed, the β-[2-(4-bromobenzyl)-phenoxy]-N,N-dimethylethylamine, is not alkylated on the 4-position of the phenoxy group.

On the other hand it is also known from FR-A-2 372 792 that ω-[2-(halogenobenzyl)-4-($C_1$-$C_5$)-alkyl-phenoxy]-N,N-dialkyl-propyl-, butyl- or pentylamines have been proposed as antidepressant agents.

According to the invention are proposed new compounds of the dichloro- and trichlorobenzyl type which are structurally different from the prior art compounds, and which are particularly interesting from a therapeutical point of view on account of (i) their affinity for water and (ii) their anti-infectious and/or antidepressant properties.

The new compounds according to the invention, which are derivatives of β-[2-(halogenobenzyl)-phenoxy]-ethylamine, are characterized in that they are selected from the group consisting of (i) N,N-dialkyl-β-[2-(polychlorobenzyl)-4-alkyl-phenoxy]-ethylamines of the general formula

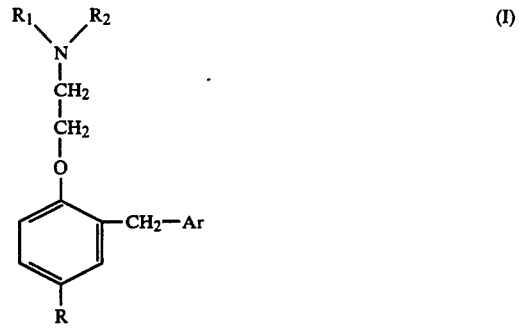

wherein
R represents a ($C_1$-$C_8$)-alkyl group having a linear or branched hydrocarbon chain;
$R_1$ and $R_2$, which may be identical or different, represent each a ($C_1$-$C_4$)-alkyl group, and
Ar represents a polychlorophenyl group of the formula

(wherein $Y_1$ is 4-Cl, $Y_2$ is H or Cl, and $Y_3$ is H or Cl, at least one of the $Y_2$ and $Y_3$ being a chlorine atom); and (ii) addition salts thereof.

Amongst the R alkyl groups which are suitable according to the invention, one can cite in particlar the $CH_3$, $CH_2CH_3$, $CH(CH_3)_2$, $C(CH_3)_3$, $CH(CH_3)CH_2CH_3$, $(CH_2)_3CH_3$, $CH_2C(CH_3)_3$, $CH_2CH(CH_3)CH_2CH_3$, $C(CH_3)_2CH_2C(CH_3)_3$, $C(CH_3)_2CH_2CH_3$ and $(CH_2)_5CH_3$ radicals.

The expression "addition salts" is understood here as meaning firstly the acid addition salts obtained by reacting the free base of formula I with inorganic or organic acids, and secondly the ammonium salts. Hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular among the acids which can be used to satisfy the said free base. Amongst the compounds useful for obtaining the ammonium salts, one can cite $XR_3$ compounds (wherein X is F, Cl, Br or I, and, $R_3$ is a ($C_1$-$C_{10}$)-alkyl group or a benzyl group).

Thus the invention is concerned with free bases of the formula I and their acid addition salts, on one hand, and with their ammonium salts of the formula

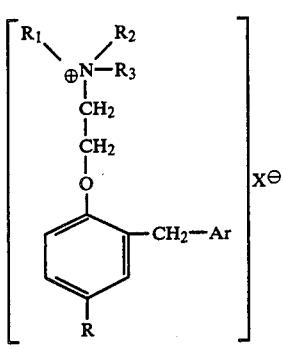

(wherein Ar, R, $R_1$, $R_2$, $R_3$ and X are as above defined), on the other hand.

The preferred compounds according to the invention are those wherein $R_1=R_2=CH$ or $CH_2CH_3$ and $Y_1$ is 4-Cl, $Y_2$ is H, and $Y_3$is 2-Cl or 3-Cl, and which are represented by the formula

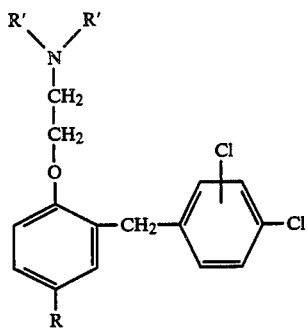

wherein R is a $(C_1-C_8)$-alkyl group, R' is $CH_3$ or $C_2H_5$; their acid addition salts, and, their ammonium salts with $XR'_3$ (wherein $R'_3$ is $CH_3$, $CH_2CH_3$ or $CH_2C_6H_5$, and X is F, Cl, Br or I). The preferred ammonium salts cited above can be represented by the formula

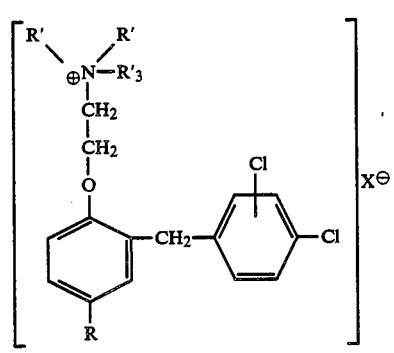

(wherein X, R, R' and $R'_3$ are as above defined, X being advantageously Cl, Br or I).

The compounds according to the invention can be prepared by a method known per se by using classical reaction mechanisms. The method which is recommended here comprises reacting a 2-(halogenobenzyl)-4-alkylphenol of the formula

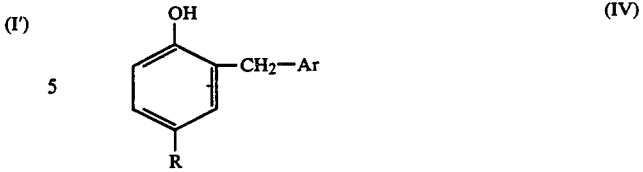

wherein Ar and R are as above defined, with a $\beta$-N,N-dialkylaminoethyl halide of the formula

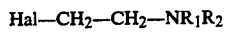

$$Hal—CH_2—CH_2—NR_1R_2 \quad (V)$$

(wherein Hal is Cl or Br, and, $R_1$ and $R_2$ are as above defined).

This reaction is advantageously carried out in an inert solvent, in particular dimethylformamid, tetrahydrofuran, for at least 5 hours at a temperature lower than or equal to the refluxing temperature, while using at least 1.1 mol of V for 1 mol of IV, the halide being preferably the chloride (Hal=Cl).

The free bases of formula I, their acid addition salts and their ammonium salts are useful as pharmaceuticals. They all present antiinfectious properties in the sense that act they according to the doses as bacteriostatic, bactericidal, fungistatic, or, fungicidal agents; in a general manner the ammonium salts are more active as antiinfectious substances than the acid addition salts, these latter being also more active than the free bases.

Moreover the free bases and their acid addition salts exhibit other beneficial effects: they act on the central nervous system as antidepressant agents and are active against enuresia. Some compounds amongst the free bases and their acid addition salts, such as for instance Example compounds 11 (B 795), 12 (B 805), 13 (B 809), 14 (B 785) and 15 (B 751), exhibit moreover beneficial spasmolytic properties. The most interesting compound, as spasmolytic agent, is the compound of Example 12 (B 805).

According to the invention a therapeutical composition is provided which is characterized in that it comprises, in association with a physiologically acceptable excipient, at least a compound of formula I or one of its addition salts, as active ingredient.

Of course in such a composition the active ingredient which is selected from the group consisting of the free bases of formula I, their non-toxic addition salts, and, if needed, mixtures thereof, is present in a pharmaceutically effective amount.

A certain number of compounds according to the invention are given non-restrictively by way of illustration in tables I, II and III hereinafter. The minimal inhibiting concentrations (MIC) of these compounds vis-a-vis a Gram+bacteria (*Staphylococcus aureus* London) a Gram-bacteria (*Escherichia coli*) and a fungus (*Candida albicans*) are given hereinafter in table IV. In table V are tabulated the MIC values of two compounds according to the invention which are particularly interesting [compound B 673 (example 26) and compound B 674 (example 29)] vis-a-vis several strains.

The strains used are those of the catalogues of the "Institut Pasteur" of Paris (abbreviation: CIP), the "Centre International de Distribution de Souches et d'Information sur les Types Microbiens de Lausanne" (abbreviation: La) and the "American Type Culture Collection" (abbreviation: ATCC).

TABLE I

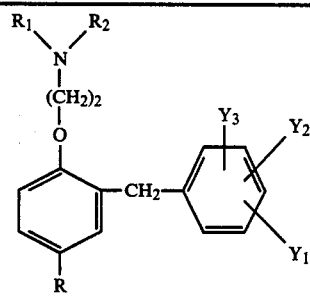

| Product | Code No | R | $R_1$ | $R_2$ | $Y_1$ | $Y_2$ | $Y_3$ | Eb(a) (°C.) |
|---|---|---|---|---|---|---|---|---|
| Ex 1 | B 715 | $CH_3$ | $C_2H_5$ | $C_2H_5$ | 4-Cl | H | 2-Cl | — |
| Ex 2 | B 776 | $CH_2CH_3$ | $C_2H_5$ | $C_2H_5$ | 4-Cl | H | 2-Cl | 180–190 |
| Ex 3 | B 770 | $CH(CH_3)_2$ | $C_2H_5$ | $C_2H_5$ | 4-Cl | H | 2-Cl | 200–206 |
| Ex 4 | B 803 | $CH(CH_3)CH_2CH_3$ | $C_2H_5$ | $C_2H_5$ | 4-CL | H | 2-CL | 172–174 |
| Ex 5 | B 680 | $C(CH_3)_3$ | $C_2H_5$ | $C_2H_5$ | 4-Cl | H | 2-Cl | 195–197 |
| Ex 6 | B 748 | $C(CH_3)_2CH_2CH_3$ | $C_2H_5$ | $C_2H_5$ | 4-CL | H | 2-Cl | 180–184 |
| Ex 7 | B 760 | $(CH_2)_3CH_3$ | $C_2H_5$ | $C_2H_5$ | 4-Cl | H | 2-Cl | 185–190 |
| Ex 8 | B 750 | $(CH_2)_5CH_3$ | $C_2H_5$ | $C_2H_5$ | 4-Cl | H | 2-Cl | 210–215 |
| Ex 9 | B 629 | $C(CH_3)_2CH_2C(CH_3)_3$ | $C_2H_5$ | $C_2H_5$ | 4-Cl | H | 2-Cl | — |
| Ex 10 | — | $CH(CH_3)_2$ | $CH_3$ | $CH_3$ | 4-Cl | H | 3-Cl | — |

Note (a): Boiling point under 0.5 mmHg (i.e. about 66.6 pascals)

TABLE II

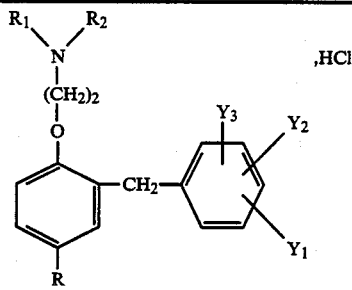

| Product | Code No | R | $R_1$ | $R_2$ | $Y_1$ | $Y_2$ | $Y_3$ | MP(a) (°C.) |
|---|---|---|---|---|---|---|---|---|
| Ex 11 | B 795 | $CH_2CH_3$ | $C_2H_5$ | $C_2H_5$ | 4-Cl | H | 2-Cl | 155–156 |
| Ex 12 | B 805 | $CH(CH_3)_2$ | $C_2H_5$ | $C_2H_5$ | 4-Cl | H | 2-Cl | 158–159 |
| Ex 13 | B 809 | $CH(CH_3)CH_2CH_3$ | $C_2H_5$ | $C_2H_5$ | 4-Cl | H | 2-Cl | 146–147 |
| Ex 14 | B 785 | $C(CH_3)_2CH_2CH_3$ | $C_2H_5$ | $C_2H_5$ | 4-Cl | H | 2-Cl | 145–150 |
| Ex 15 | B 751 | $C(CH_3)_2CH_2C(CH_3)_3$ | $C_2H_5$ | $C_2H_5$ | 4-Cl | H | 2-Cl | 149–150 |
| Ex 16 | — | $C(CH_3)_3$ | $CH_3$ | $CH_3$ | 4-Cl | H | 2-Cl | — |
| Ex 17 | — | $CH(CH_3)_2$ | $CH_3$ | $CH_3$ | 4-Cl | H | 3-Cl | — |
| Ex 18 | — | $CH_3$ | $C_2H_5$ | $C_2H_5$ | 4-Cl | H | 2-Cl | — |
| Ex 19 | — | $C(CH_3)_3$ | $CH_3$ | $CH_3$ | 4-Cl | 3-Cl | 2-Cl | — |
| Ex 20 | — | $C(CH_3)_2CH_2CH_3$ | $CH_3$ | $CH_3$ | 4-Cl | H | 3-Cl | — |

Note (a): instantaneous melting point.

TABLE III

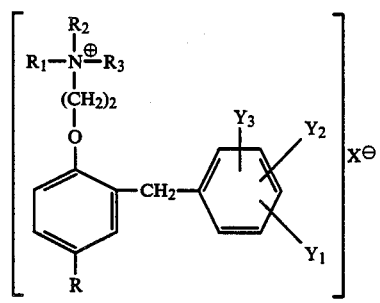

| Product | Code No | R | $R_1$ | $R_2$ | $R_3$ | $Y_1$ | $Y_2$ | $Y_3$ | X | MP(a) (°C.) |
|---|---|---|---|---|---|---|---|---|---|---|
| Ex 21 | B 794 | $C(CH_3)_2CH_2CH_3$ | $C_2H_5$ | $C_2H_5$ | $CH_3$ | 4-Cl | H | 2-Cl | I | 138–140 |
| Ex 22 | B 622 | $C(CH_3)_2CH_2C(CH_3)_3$ | $C_2H_5$ | $C_2H_5$ | $CH_3$ | 4-Cl | H | 2-Cl | I | 157–158 |
| Ex 23 | B 798 | $C(CH_3)_2CH_2CH_3$ | $C_2H_5$ | $C_2H_5$ | $(CH_2)_3CH_3$ | 4-Cl | H | 2-Cl | Br | 104–108 |
| Ex 24 | B 808 | $C(CH_3)_2CH_2C(CH_3)_3$ | $C_2H_5$ | $C_2H_5$ | $(CH_2)_3CH_3$ | 4-Cl | H | 2-Cl | Br | 167–168 |

TABLE III-continued

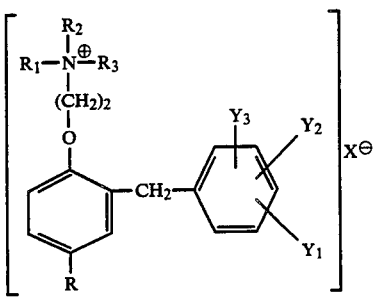

| Product | Code No | R | $R_1$ | $R_2$ | $R_3$ | $Y_1$ | $Y_2$ | $Y_3$ | X | MP(a) (°C.) |
|---|---|---|---|---|---|---|---|---|---|---|
| Ex 25 | B 852 | $C(CH_3)_3$ | $C_2H_5$ | $C_2H_5$ | $(CH_2)_3CH_3$ | 4-Cl | H | 2-Cl | Br | 124–125 |
| Ex 26 | B 673 | $CH_3$ | $C_2H_5$ | $C_2H_5$ | $CH_2C_6H_5$ | 4-Cl | H | 2-Cl | Cl | 134–136 |
| Ex 27 | B 791 | $CH_2CH_3$ | $C_2H_5$ | $C_2H_5$ | $CH_2C_6H_5$ | 4-Cl | H | 2-Cl | Cl | 125–130 |
| Ex 28 | B 774 | $CH(CH_3)_2$ | $C_2H_5$ | $C_2H_5$ | $CH_2C_6H_5$ | 4-Cl | H | 2-Cl | Cl | 116–118 |
| Ex 29 | B 674 | $C(CH_3)_3$ | $C_2H_5$ | $C_2H_5$ | $CH_2C_6H_5$ | 4-Cl | H | 2-Cl | Cl | 120–125 |
| Ex 30 | B 768 | $C(CH_3)_2CH_2CH_3$ | $C_2H_5$ | $C_2H_5$ | $CH_2C_6H_5$ | 4-Cl | H | 2-Cl | Cl | 132–135 |
| Ex 31 | B 773 | $(CH_2)_3CH_3$ | $C_2H_5$ | $C_2H_5$ | $CH_2C_6H_5$ | 4-Cl | H | 2-Cl | Cl | 126–128 |
| Ex 32 | B 775 | $(CH_2)_5CH_3$ | $C_2H_5$ | $C_2H_5$ | $CH_2C_6H_5$ | 4-Cl | H | 2-Cl | Cl | 125–127 |
| Ex 33 | B 617 | $C(CH_3)_2CH_2C(CH_3)_3$ | $C_2H_5$ | $C_2H_5$ | $CH_2C_6H_5$ | 4-Cl | H | 2-Cl | Cl | 181–183 |
| Ex 34 | — | $CH_3$ | $CH_3$ | $CH_3$ | $CH_2CH_3$ | 4-Cl | H | 2-Cl | Cl | — |
| Ex 35 | — | $CH(CH_3)CH_2CH_3$ | $CH_3$ | $CH_3$ | $CH_2C_6H_5$ | 4-Cl | H | 3-Cl | Cl | — |
| Ex 36 | — | $CH(CH_3)_2$ | $CH_3$ | $CH_3$ | $CH_2C_6H_5$ | 4-Cl | H | 3-Cl | Cl | — |
| Ex 37 | — | $C(CH_3)_3$ | $CH_3$ | $CH_3$ | $CH_2C_6H_5$ | 4-Cl | H | 3-Cl | Cl | — |
| Ex 38 | — | $C(CH_3)_2CH_2C(CH_3)_3$ | $CH_3$ | $CH_3$ | $CH_2CH_3$ | 4-Cl | H | 2-Cl | F | — |
| Ex 39 | — | $CH(CH_3)CH_2CH_3$ | $CH_3$ | $CH_3$ | $CH_2CH_3$ | 4-Cl | H | 2-Cl | F | — |
| Ex 40 | — | $C(CH_3)_2CH_2CH_3$ | $C_2H_5$ | $C_2H_5$ | $CH_2CH_3$ | 4-Cl | 3-Cl | 2-Cl | F | — |

Note: (a) instantaneous melting point

TABLE IV

| | | MIC (µg/ml) | | |
|---|---|---|---|---|
| Product | Code No | $G^+$ | $G^-$ | C |
| Ex 1 | B 715 | 12.5 | 50 | — |
| Ex 2 | B 776 | 64 | — | 64 |
| Ex 3 | B 770 | 16 | — | 8 |
| Ex 4 | B 803 | 32 | — | 16 |
| Ex 5 | B 680 | 50 | — | — |
| Ex 6 | B 748 | 8 | — | 16 |
| Ex 7 | B 760 | 64 | 64 | 64 |
| Ex 8 | B 750 | 64 | 64 | 64 |
| Ex 9 | B 629 | 25 | — | — |
| Ex 10 | — | 16 | 64 | — |
| Ex 11 | B 795 | 8 | — | 8 |
| Ex 12 | B 805 | 4 | — | 4 |
| Ex 13 | B 809 | 8 | — | 0.5 |
| Ex 14 | B 785 | 8 | 64 | 4 |
| Ex 15 | B 751 | 16 | — | — |
| Ex 21 | B 794 | 0.125 | 8 | 0.5 |
| Ex 22 | B 622 | 0.125 | 64 | 0.25 |
| Ex 23 | B 798 | 0.06 | 4 | 0.25 |
| Ex 24 | B 808 | 0.015 | 16 | 1 |
| Ex 26 | B 673 | 0.25 | 32 | 4 |
| Ex 27 | B 791 | 0.125 | 8 | 0.5 |
| Ex 28 | B 774 | 0.015 | 8 | 0.25 |
| Ex 29 | B 674 | 0.015 | 4 | 0.125 |
| Ex 30 | B 768 | 0.004 | 4 | 0.25 |
| Ex 31 | B 773 | 0.031 | 4 | 0.125 |
| Ex 32 | B 775 | 0.125 | 16 | 0.5 |
| Ex 33 | B 617 | 0.03 | — | 1 |

Notes:
$G^+$ = Gram$^+$ strain: *Staphylococcus aureus* London CIP A.238
$G^-$ = Gram$^-$ strain: *Escherichia coli* CIP 54.8
C = fungus strain: *Candida albicans* CIP 1180

TABLE V

| | MIC (in µg/ml) vis-a-vis several strains | |
|---|---|---|
| STRAINS | Example 26 (B 673) | Example 29 (B 674) |
| *Staphylococcus aureus* ATCC 6538 P | 0.78 | 0.78 |
| *Streptococcus pyogenes* la 147 | 0.78 | 0.78 |
| *Streptococcus pyogenes* CIP A.241 | 0.78 | 0.78 |
| *Streptococcus pyogenes* CIP 56.42 | 0.78 | 0.78 |
| *Streptococcus faecalis* CIP 53.152 | 3.125 | 0.78 |
| *Diplococcus pneumoniae* la 209 | 1.56 | 0.78 |
| *Bacillus subtilis* ATCC 6633 | 1.56 | 0.78 |
| *Corynebacterium diphteriae* CIP A.102 | 25 | 3.125 |
| *Branhamella catarrhalis* la 987 | 0.78 | 0.78 |
| *Neisseria gonorrhoeae* CIP A.52 | 0.78 | 0.78 |
| *Haemophilus influenzae* CIP 5293 | 0.78 | 0.78 |
| *Klebsiella pneumoniae* la 433 | 25 | 6.25 |
| *Streptococcus pyogenes* CIP 5641 | 0.78 | 0.78 |
| *Neisseria meningitidis* CIP 7310 | 0.78 | 0.78 |
| *Listeria monocytogenes* CIP 54153 | 1.56 | 0.78 |

In a general manner, the compounds according to the invention exhibit a low toxicity and are well tolerated by the organism. Table VI given hereinafter shows in particular that the ammonium salts of compounds according to the formula I are less toxic than the ammonium salts previously known as anti-infectious agents.

TABLE VI

| | TOXICITY | |
|---|---|---|
| Product | Code No | LD-50 mice (mg/kg) |
| Ex 23 | B 798 | >1 000 |
| Ex 26 | B 673 | >1 000 |
| Ex 27 | B 791 | 850 |
| Ex 29 | B 674 | >1 000 |
| Ex 30 | B 768 | >1 000 |
| Ex 31 | B 773 | >1 000 |
| A-1 (a) | — | 550 |
| A-2 (b) | — | 750 |

Notes:
(a): benzalkonium chloride
(b): cetrymonium chloride

Further advantages and characteristics of the invention will be understood more clearly on reading the following description of preparative examples which do not imply a limitation but are given by way of illustration.

PREPARATION I

Preparation of β-[2-(2,4-dichlorobenzyl)-4-tertiobutylphenoxy]-N,N-diethyl-ethylamine

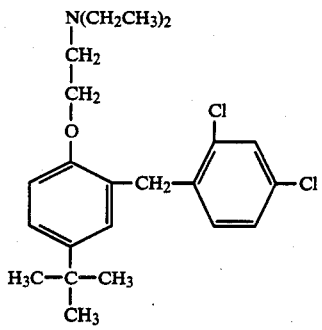

(example 5; Code No: B 680);
alternative nomenclature: 2-(2-diethylaminoethoxy)-5-tertiobutyl-2',4'-dichlorodiphenylmethane.

In a reactor, a mixture consisting of 1 mol (309.18 g) of 2-(2,4-dichlorobenzyl)-4-tertiobutylphenol, 2.4 mols of $K_2CO_3$, 2 liters of dimethylformamid and 1.2 mols of 2-chloro-N,N-diethylethylamine hydrochloride, is made to react, under stirring, for 15 hours at 120° C.

The reaction mixture is poured into a saline solution (water saturated with NaCl), extracted with $CHCl_3$; the chloroform phase is washed with water, dried and evaporated under vacuum. By distillation under vacuum of the evaporation residue, B 680 is obtained with a yield of 76.1%.

$Eb_{0.5\ mmHg} = 195°-197°$ C.

PREPARATION II

Preparation of N,N-diethyl-N-{2-[2-(2,4-dichlorobenzyl)-tertiobutyl-phenoxy]-ethyl}-N-benzylammonium chloride

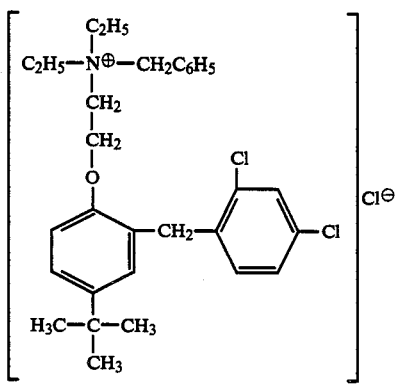

(Example 29; Code No 674).

In a reactor 1 mol (408.25 g) of β-[2-(2,4-dichlorobenzyl)-4-tertiobutylphenoxy]-N,N-diethylethylamine is made to react with 1.25 mols of benzyl chloride, for 17 h at 90°-100° C., under stirring. After cooling to room temperature (15°-20° C.), the reaction mixture is washed with diethylether in order to obtain a precipitate which is washed with hexane then acetone at 15°-20° C. By recrystallization B 674 is obtained with a yield of 85.8%.

$MP_{inst} = 120°-125°$ C.

PREPARATION III

Preparation of β-[2-(2,4-dichlorobenzyl)-4-(1,1-dimethylpropyl)-phenoxy]-N,N-diethylethylamine hydrochloride (Example 14; Code No B 785).

A HCl gas stream is introduced into a solution of 1 mol (422.31 g) of β-[2-(2,4-dichlorobenzyl)-4-(1,1-dimethylpropyl)-phenoxy]-N,N-diethylethylamine (Example 6; Code No B 748) in 800 ml of anhydrous diethylether; After reaction the HCl gas bubbling is stopped and the mixture thus obtained is evaporated to dryness under vacuum, and the evaporation residue is taken up with anhydrous diethylether. A precipitate is formed which is washed with anhydrous diethylether. B 785 is obtained with a yield of 83.3%.

$MP_{inst} = 145°-150°$ C.

PREPARATION IV

Preparation of N,N-diethyl-N-{2-[2-(2,4-dichlorobenzyl)-4-(1,1-dimethylpropyl)-phenoxy]-ethyl}-N-methylammonium iodide (Example 21; Code No B 794)

A mixture of 1 mol (422.31 g) of β-[2-(2,4-dichlorobenzyl)-4-(1,1-dimethylpropyl)-phenoxy]-N,N-diethylethylamine, 1.25 mols of $ICH_3$ and 1.2 liters of anhydrous acetone is made to react for 2 h at 45° C. under stirring. After cooling, the reaction mixture is poured into cold (15° C.) $CH_3CO_2C_2H_5$. A precipitate is obtained. By recrystallization from a $CH_3CO_2C_2H_5$—$C_2H_5OH$ (98:2) v/v mixture, B 794 is obtained with a yield of 62.4%.

$MP_{inst} = 138°-140°$ C.

PREPARATION V

Preparation of N,N-diethyl-N-{2-[2-(2,4-dichlorobenzyl)-4-(1,1-dimethylpropyl)-phenoxy]-ethyl}-N-butylammonium bromide (Example 23; Code No B 798)

One mol (422.31 g) of β-[2-(2,4-dichlorobenzyl)-4-(1,1-dimethylpropyl)-phenoxy]-N,N-diethylethylamine is reacted with 1.25 mols of 1-bromobutane, for 15 h at 100° C., under stirring.

After cooling, the reaction mixture is washed with hexane then diethylether to give a precipitate. After washing of this precipitate at 30° C. with $CH_3CO_2C_2H_5$, B 798 is obtained with a yield of 20.4%

$MP_{inst} = 104°-108°$ C.

What is claimed is:

1. A β-[2-(halogenobenzyl)-phenoxy]-ethylamine derivative selected from the group consisting of:
   (i) N,N-dialkyl-β-[2-(polychlorobenzyl)-4-alkyl-phenoxy]-ethylamines of the general formula

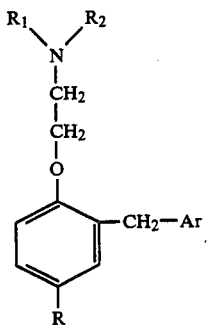
(I)

wherein R represents a $C_1$–$C_8$-alkyl group having a linear or branched hydrocarbon chain, $R_1$ and $R_2$, can be identical or different and each represent a $C_1$–$C_4$-alkyl group, and Ar represents a polychlorophenyl group of the formula

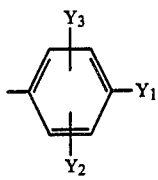
(II)

wherein $Y_1$ is Cl, $Y_2$ is H or Cl, and $Y_3$ is H or Cl, and wherein at least one of $Y_2$ and $Y_3$ is Cl; and
(ii) addition salts thereof.

2. A compound according to claim 1 in which R is $CH_3$, $CH_2CH_3$, $CH(CH_3)_2$, $C(CH_3)_3$, $CH(CH_3)CH_2CH_3$, $C(CH_3)_2CH_2CH_3$, $(CH_2)_3CH_3$, $(CH_2)_5CH_3$, $CH_2C(CH_3)_3$, $CH_2CH(CH_3)CH_2CH_3$ or $C(CH_3)_2CH_2C(CH_3)_3$.

3. A compound according to claim 1 which is selected from the group consisting of ammonium salts of the formula

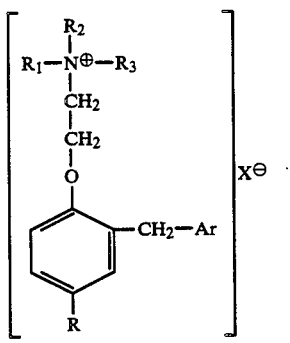
(I')

wherein Ar, R, $R_1$ and $R_2$ are defined as indicated in claim 1, $R_3$ is a $C_1$–$C_{10}$-alkyl or benzyl group, and, X is F, Cl, Br or I.

4. A compound according to claim 1, which is selected from the group consisting of
(i) compounds of the formula

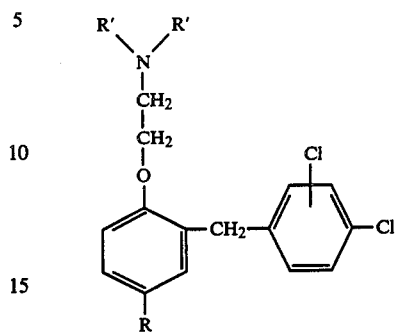
(III)

wherein R' is $CH_3$ or $C_2H_5$ and R is a $C_1$–$C_8$-alkyl group; and
(ii) acid addition salts thereof.

5. A compound according to claim 1 which is selected from the group consisting of ammonium salts of the formula

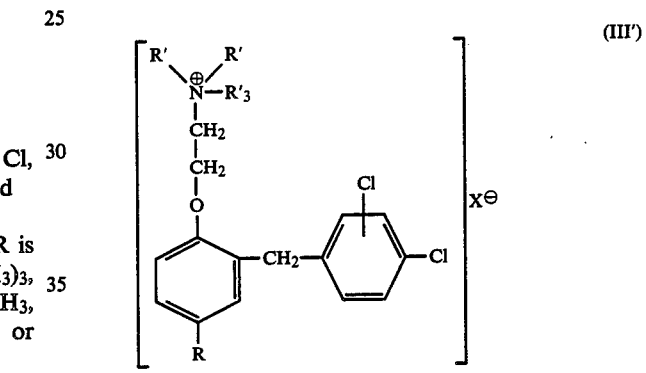
(III')

wherein R' is $CH_3$ or $C_2H_5$, R is a $C_1$–$C_8$-alkyl group, $R'_3$ is $CH_3$, $CH_2CH_3$ or $CH_2C_6H_5$, and X is F, Cl, Br or I.

6. β-[2-(2,4-Dichlorobenzyl-4-t-butylphenoxy]-N,N-diethylethylamine and its addition salts.

7. β-[2-(2-(2,4-Dichlorobenzyl)-4-(1,1-dimethylpropyl)-phenoxy]-N,N-diethyl-ethylamine and its addition salts.

8. N,N-Diethyl-N-{2-[2-(2,4-dichlorobenzyl)-4-t-butylphenoxy]-ethyl}-N-benzylammonium chloride.

9. β-[2-(2,4-Dichlorobenzyl)-4-(1,1,3,3-tetramethylbutyl)-phenoxy]-N,N-diethyl-ethylamine and its addition salts.

10. N,N-Diethyl-N-{2-[2-(2,4-dichlorobenzyl)-4-(1,1,3,3-tetramethylbutyl)-phenoxy]-ethyl}-N-benzylammonium chloride.

11. A therapeutical composition comprising, in association with a physiologically acceptable excipient, a pharmaceutically effective amount of a compound according to claim 1.

* * * * *